United States Patent
Orbay et al.

(10) Patent No.: US 6,706,046 B2
(45) Date of Patent: Mar. 16, 2004

(54) INTRAMEDULLARY FIXATION DEVICE FOR METAPHYSEAL LONG BONE FRACTURES AND METHODS OF USING THE SAME

(75) Inventors: Jorge L. Orbay, Miami, FL (US); Javier Castañeda, Miami, FL (US)

(73) Assignee: Hand Innovations, Inc., Miami, FL (US)

( * ) Notice: Subject to any disclaimer, the term of this patent is extended or adjusted under 35 U.S.C. 154(b) by 0 days.

(21) Appl. No.: 10/315,787

(22) Filed: Dec. 10, 2002

(65) Prior Publication Data
US 2003/0083661 A1 May 1, 2003

Related U.S. Application Data

(63) Continuation-in-part of application No. 10/159,611, filed on May 30, 2002, which is a continuation-in-part of application No. 09/495,854, filed on Feb. 1, 2000, now Pat. No. 6,358, 250, and a continuation-in-part of application No. 09/524, 058, filed on Mar. 13, 2000, now Pat. No. 6,364,882, and a continuation-in-part of application No. 09/735,228, filed on Dec. 12, 2000, now Pat. No. 6,440,135.

(51) Int. Cl.[7] .......................... A61B 17/80; A61B 17/72
(52) U.S. Cl. ............................ 606/69; 606/62
(58) Field of Search .................. 606/60, 62, 64, 606/67, 69–71, 72, 73, 86

(56) References Cited
U.S. PATENT DOCUMENTS 4,733,654 A * 3/1988 Marino ................... 606/64
5,356,410 A * 10/1994 Pennig .................... 606/62
5,578,035 A 11/1996 Lin .......................... 606/68
6,146,384 A 11/2000 Lee et al. ................. 606/73
6,238,395 B1 5/2001 Bonutti .................... 606/60
6,270,499 B1 8/2001 Leu et al. ................. 606/64
6,527,775 B1 3/2003 Warburton ............... 606/62
2003/0105461 A1 6/2003 Putnam .................... 606/69

* cited by examiner

Primary Examiner—Kevin Shaver
Assistant Examiner—Michael B. Priddy
(74) Attorney, Agent, or Firm—Gordon & Jacobson, P.C.

(57) ABSTRACT

A fixation system includes a device having a nail portion and a plate portion, preferably horizontally and vertically offset relative to the nail portion by a neck portion. The nail portion includes threaded screw holes, and the plate portion includes longitudinally displaced peg holes, each of which is adapted to orient a peg in a different orientation from the others. The system also includes unicortical screws having a reasonably large head adapted to seat against the outer surface of the bone and a threaded shaft adapted to engage in the screw holes, and pegs adapted to engage in the peg holes. Bone is clamped between the nail portion and the head of the unicortical screws. The pegs provide stabilization and support for subchondral fragments. Moreover, as the pegs preferably enter the subchondral fragments from a plurality of directions, additional fixation of the device into the bone is provided.

29 Claims, 6 Drawing Sheets

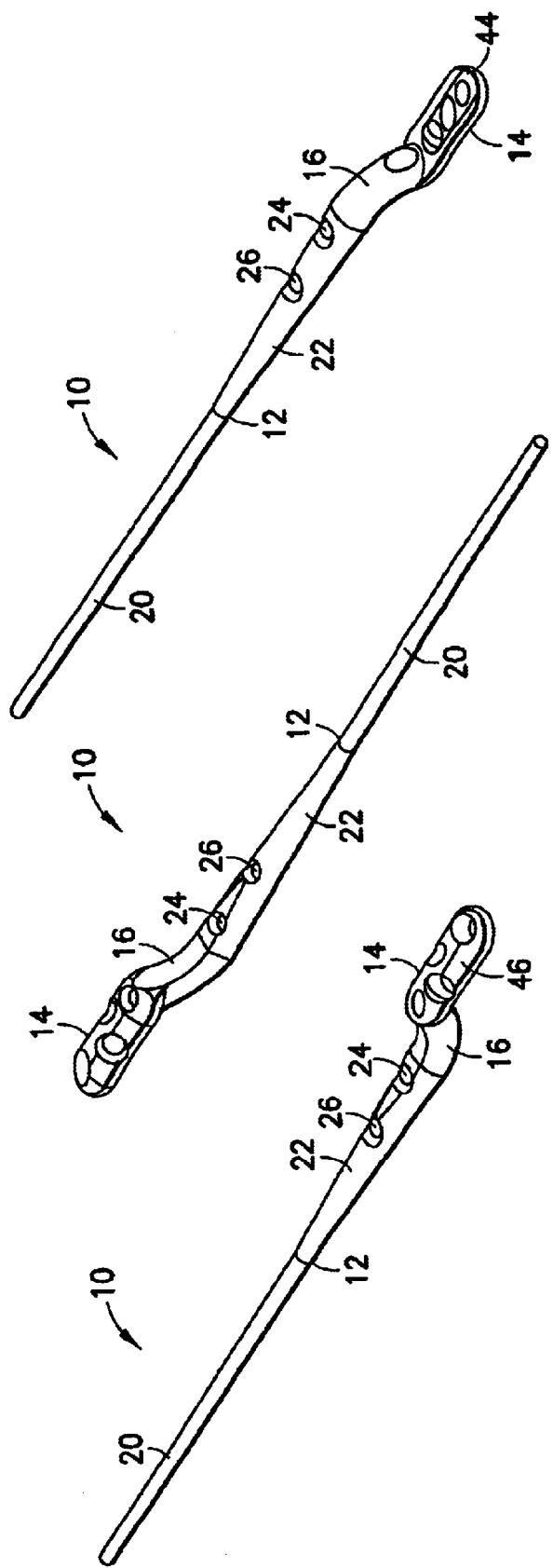

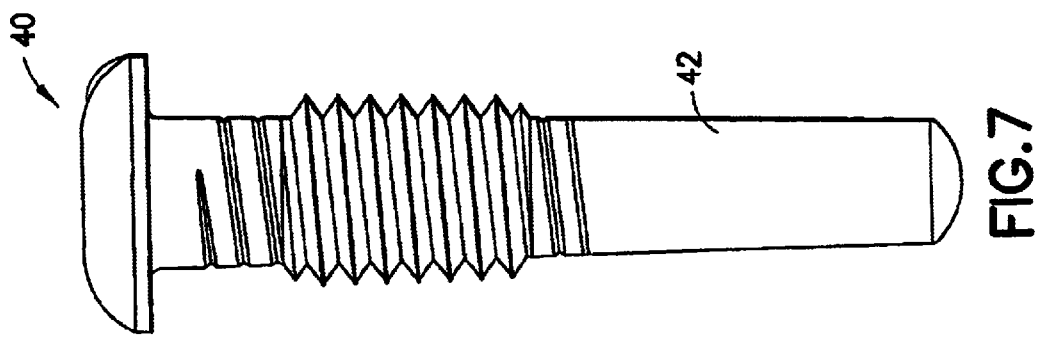
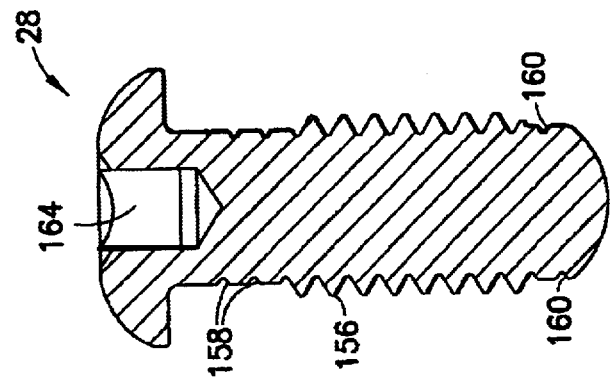
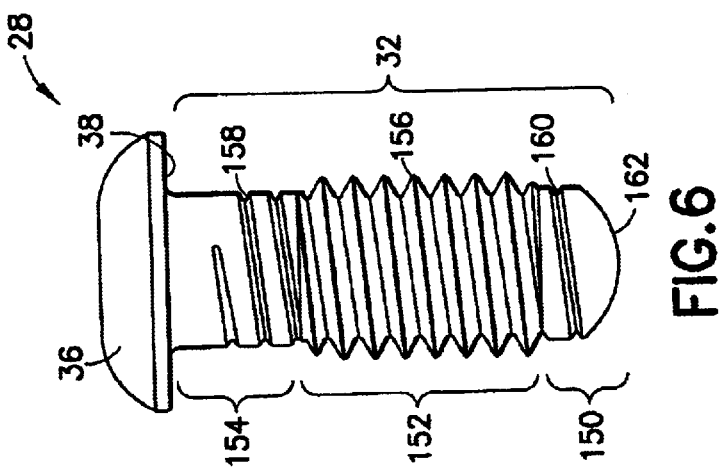

INTRAMEDULLARY FIXATION DEVICE FOR METAPHYSEAL LONG BONE FRACTURES AND METHODS OF USING THE SAME

This application is a continuation-in-part of U.S. Ser. No. 10/159,611, filed May 30, 2002, which is a continuation-in-part of U.S. Ser. No. 09/495,854, filed Feb. 1, 2000, now U.S. Pat. No. 6,358,250, U.S. Ser. No. 09/524,058, filed Mar. 13, 2000, now U.S. Pat. No. 6,304,882, and U.S. Ser. No. 09/735,228, filed Dec. 12, 2000, now U.S. Pat. No. 6,440,135, all of which are hereby incorporated by reference herein in their entireties.

BACKGROUND OF THE INVENTION

1. Field of the Invention

This invention relates broadly to surgical devices. More particularly, this invention relates to cross-fastened intramedullary implants for the fixation of bone fractures.

2. State of the Art

Severe long bone fractures are often treated with plating. In plating, a relatively large incision is made at the location of the fracture, musculature and tendons are displaced from the bone to expose the bone surface, and a bone plate is fixedly attached to one or more pieces of the fractured bone in a manner which, ideally, supports and stabilizes the fracture for healing. Due to the relatively invasive nature of the procedure required to implant the plate, plating is generally reserved for fractures which cannot be treated with a less invasive method of immobilization.

Less complicated fractures are often treated with casting or wires. However, such conservative treatment may not provide the stabilization and support necessary for desirable recovery. Yet, the operative procedure of plating is often too invasive for the relative non-severity of the fracture. Moreover, conventional plating can result in tendon irritation and skin necrosis, and may require extensive periosteal stripping in order to apply the plate on the bone surface. As such, many of the less displaced fractures, and particularly metaphyseal fractures (fractures at the end of the long bones), remain undertreated.

By way of example, a Colles' fracture, which results from compressive forces being placed on the distal radius bone, and which causes backward displacement of the distal fragment and radial deviation of the hand at the wrist, is treated with a dorsal plate when there is a significant degree of displacement. However, a less-displaced Colles' fracture is commonly undertreated due to the hesitancy of physicians to prescribe operative and invasive treatment. If not properly treated, such a fracture results in permanent wrist deformity. It is therefore important to align the fracture and fixate the bones relative to each other so that proper healing may occur.

In addition, there is no relatively minimally invasive procedure to treat fractures occurring at the metaphysis and that also provides the desired reduction and immobilization for such fractures.

Furthermore, there is no relatively minimally invasive procedure to treat distal radius fractures that provides the stability generally obtained by more invasive procedures, such as open reduction and internal fixation.

SUMMARY OF THE INVENTION

It is therefore an object of the invention to provide a relatively minimally invasive treatment which provides stabilization and support to long bone fractures.

It is another object of the invention to provide a relatively minimally invasive treatment which provides stabilization and support to metaphyseal fractures.

It is a further object of the invention to provide a implant which is fixedly held within the medullary canal of a long bone.

In accord with these objects, which will be discussed in detail below, a fixation system includes a device having a proximal nail portion and a distal plate portion, preferably horizontally and vertically offset relative to the nail portion by a neck portion. The nail portion includes a tapered end which is resilient, and a relatively rigid distal portion larger in diameter. For treatment of distal radius fractures, the distal portion of the nail portion preferably includes two threaded screw holes, and the plate portion has a low, narrow profile and includes three longitudinally displaced peg holes, each of which is adapted to orient a peg in a different orientation from the others. The plate portion also includes a threaded guide hole at which a guide can be stabilized with a screw in order to drill holes in alignment with the screw holes and pegs holes. The system also includes unicortical machine screws having a reasonably large head adapted to seat against the outer surface of the bone and a threaded shaft adapted to engage in the screw holes, and pegs adapted to engage in the peg holes.

In use, a relatively small incision is made in the skin, and the tapered end of the nail portion of the device is introduced percutaneously through the incision and through the fracture location into the medullary canal of the bone. The plate portion of the device is then maneuvered against a surface of the bone. The guide is coupled to the guide hole and the screw holes and peg holes are drilled. It is noted that the screw holes need only be drilled through the near side of the cortical bone, and not through the nail portion or the far side of the cortical bone.

The unicortical screws are then introduced through drilled holes and into the screw holes in the nail portion. The screws are tightened to pull the nail portion against the inner surface of the cortical bone. As the screws are tightened, the nail portion is pulled against the inner cortex and is automatically aligned with the axis of the bone. Thus, the plate portion is also thereby provided in a proper orientation for support of the metaphyseal area. In addition, as the screw heads are relative large, the bone is clamped between the screw heads and the nail portion. As a result, stability is increased. Alternatively, a combination of unicortical screws and bicortical screws can be used through the cortical screw holes.

The fracture at the metaphyseal portion of the bone is then reduced, and pegs are introduced through the drilled holes until the heads of the peg thread into the peg holes of the plate portion of the device. The pegs provide stabilization and support for subchondral fragments. Moreover, as the pegs preferably enter the subchondral fragments from a plurality of directions, additional fixation of the device into the bone is provided.

The fixation system permits a minimally invasive treatment of long bone fractures that may otherwise be undertreated. In addition, such fixation is very stable due to the clamping of the bone between the large screw heads and the device. Moreover, the large screw heads distribute the stress on the bone over a relatively large surface area on the outer surface of the cortical bone.

The fixation system can be adapted to treatment of fractures at multiple sites. For example, the distal radius, the proximal humerus, the distal femur, the proximal tibia, the distal tibia, and the hip are all suitable for application of the system of the invention.

Additional objects and advantages of the invention will become apparent to those skilled in the art upon reference to the detailed description taken in conjunction with the provided figures.

BRIEF DESCRIPTION OF THE DRAWINGS

FIG. 1 is a distal end top perspective view of the fixation device of the invention;

FIG. 2 is a proximal end top perspective view of the fixation device of the invention;

FIG. 3 is a distal end bottom perspective view of the fixation device of the invention;

FIG. 6 is a side view of a unicortical machine screw in accord with the system of the invention;

FIG. 6A is a longitudinal section view of the unicortical screw of FIG. 6;

FIG. 7 is a side view of a bicortical machine screw in accord with the system of the invention;

DETAILED DESCRIPTION OF THE PREFERRED EMBODIMENTS

Turning now to FIGS. 1 through 5, a fixation device 10 for the treatment of a fracture at an end of a long bone, i.e., a metaphyseal fracture, is provided. The device 10 is preferably made of metal, e.g., titanium or stainless steel, and includes an intramedullary nail portion 12 and a plate portion 14 that is preferably horizontally and vertically offset relative to the nail portion at a neck portion (or transition zone) 16. As such, the nail portion 12 and the plate portion 14 are fixed in a parallel, but non-coaxial relationship, with the plate portion 14 longitudinally displaced relative to the nail portion 12.

Figure 4:
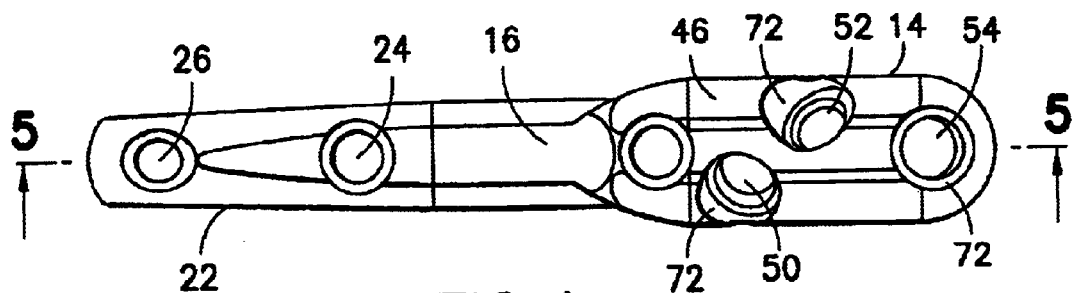
FIG. 4 is a broken top view of the fixation device of the invention.
Figure 5:
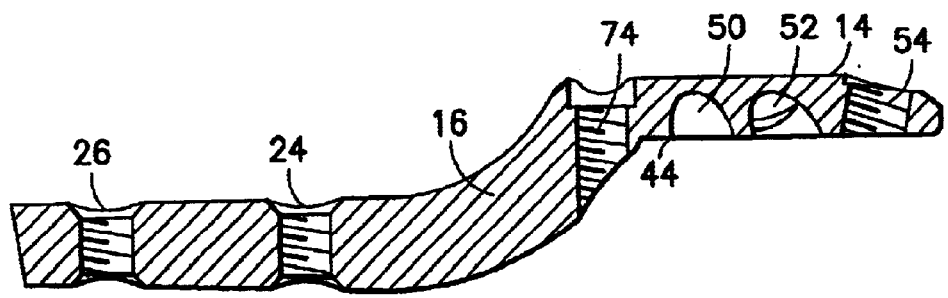
FIG. 5 is a broken longitudinal section view taken along line 5—5 in FIG. 4.

The nail portion 12 is preferably substantially circular in cross section and includes a tapered resilient (flexible) section 20, and a relatively rigid section 22 generally substantially larger in diameter adjacent the shoulder portion 16. The rigid section 22 preferably tapers toward and into the resilient section 20. Referring to FIGS. 4 and 5, the rigid section 22 of the nail portion 12 preferably includes two threaded screw holes 24, 26 preferably extending vertically through the diameter of the nail portion 12 and longitudinally displaced along the length of the rigid section 22. The screw holes 24, 26 are adapted to receive machine screws 28, 30 (FIG. 10).

Figure 10:
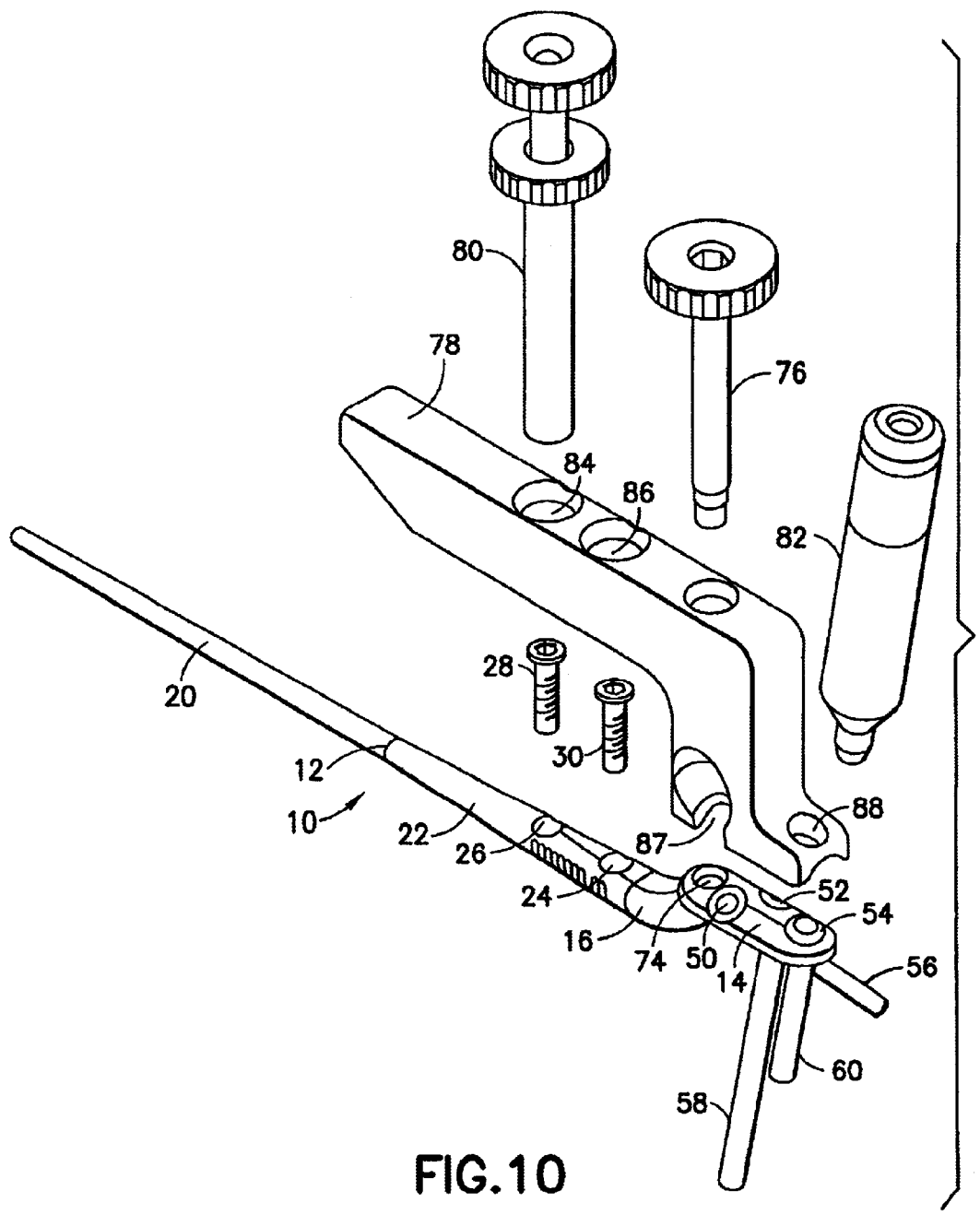
FIG. 10 is an exploded perspective view of the system of the invention in combination with a jig and drill guides.

Referring to FIGS. 6, 6A and 10, the machine screws 28, 30 are preferably unicortical in design. That is, the shaft 32 of each screw is selected in length (for the particular bone being treated) to extend through a near cortex of the bone and to thread into the screw holes 24, 26 of the nail portion 12, but preferably not to extend to the far cortex of the bone. The shaft 32 includes a tip portion 150, a body portion 152, and clearance portion 154. The body portion 152 includes threads 156 adapted to engage in the screw holes 24, 26. In the clearance portion 154, the shaft is relatively smooth, but has a shallow thread channel 158 extending therein which is continuous with and the same pitch as threads 156. The thread channel 158 is sized to accommodate the threads in screw holes 24, 26. The tip portion 150 is preferably also relatively smooth, but slightly smaller in diameter than the clearance portion 154; e.g., a 0.098 inch diameter at the clearance portion 154 versus a 0.095 inch diameter at the tip portion 150. In addition, the tip portion 150 preferably also has a shallow thread channel 160 extending therein which is continuous with and the same pitch as threads 156. The tip portion 150 preferably also has a relatively blunt end 162, as the screw is not intended to tap into bone. In addition, each screw 28 has a reasonably large head 36 with a substantially flat undersurface 38 adapted to contact bone and distribute load and stress, and a driver receiving slot 164.

As an alternative to providing solely unicortical screws 28, a combination of unicortical screws 28 and relatively longer bicortical screws 40, which preferably have a relatively long tip portion 42 adapted to extend to or even into the far cortex, can be used (FIG. 7).

Referring back to FIGS. 1 through 5, the plate portion 14 is substantially rigid and has a low and narrow profile. The plate portion 14 has a slightly concave bottom surface 44 (adapting the plate portion to the anatomy) and a slightly convex upper surface 46 (reducing potential irritation of tendons and other tissue). The concave and convex surfaces 44 and 46 may be defined by facets approximating curved surfaces. The plate portion 14 also includes preferably three longitudinally displaced, threaded peg holes 50, 52, 54, each of which is preferably adapted to orient a respective peg 56, 58, 60 (FIGS. 8 and 10) in a different orientation from the others; i.e., the axes of the peg holes are oblique relative to each other. The threads of the peg holes 50, 52, 54 may be of a different pitch than the threads in screw holes 24, 26; the pitches or each are independent.

Figure 8:
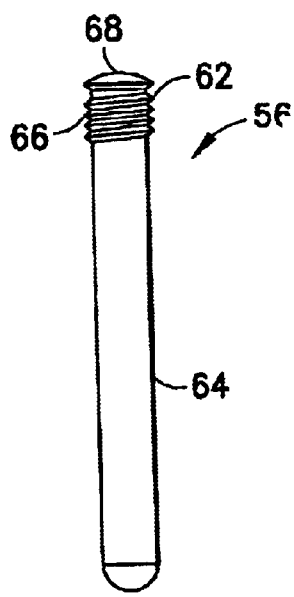
FIG. 8 is a side view of a fixed-angle peg in accord with the system of the invention.
Figure 9:
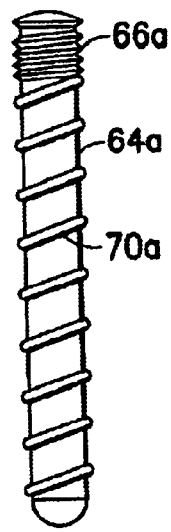
FIG. 9 is a side view of an alternative threaded fixed-angle peg in accord with the system of the invention.

Referring to FIG. 8, each peg, e.g., peg 56, includes a head 62 and a shaft 64. The head 62 has external threads 66 adapted to engage within the threaded peg holes 50, 52, 54, and a slot 68 for receiving a driver. Thus, the head 62 of the peg 56 (unlike typical screws) is adapted to threadably engage in a respective peg hole generally only in alignment with the axis through the respective peg hole. Thus, such peg systems are often referred to as 'fixed angle' devices. The shaft 64 is preferably smaller in diameter than the head 62, and also preferably non-threaded. However, referring to FIG. 9, the shaft 64a may optionally be provided with threads 70a. Such threads on the shaft are preferably of a different pitch than the threads 66a about the head of the peg. As another alternative, multidirectional pegs (which may be angled relative to the peg hole axis) and peg holes adapted therefor can also be used, as described in co-owned and co-pending U.S. Ser. No. 10/307,796, Dec. 2, 2002, which is hereby incorporated by reference herein in its entirety.

Referring to FIGS. 4, 5, and 10, in a preferred embodiment for a left-hand device 10, peg hole 50 is adapted to orient a first peg 56 approximately 41° laterally and approximately 25° relative to a line normal to the lower surface 44 of the plate portion 14 in a direction away from the nail portion 12; peg hole 52 is adapted to orient a second peg 58 approximately 41° laterally (in a direction opposite first peg 40) and approximately 15° relative to a line normal to the lower surface 44 of the plate portion 14 in a direction away from the nail portion 12; and peg hole 54 is adapted to orient a third peg 60 in the plane of the plate and nail portions 12, 14 and approximately 10° toward the nail portion 12. It is appreciated that the lateral angles are preferably opposite for a right-hand device. It is preferable that the laterally extending first and second pegs 56, 58 be substantially longer than the distal third peg 60. In alternate arrangement, the peg holes and pegs can be provided in a fanned arrangement or otherwise, particularly where one or more multidirectional pegs, as described in previously incorporated co-pending U.S. Ser. No. 10/307,796, are used. In addition, the peg holes 50, 52, 54 preferably each include a countersink portion 72 adapted to permit the heads 62 of the pegs to be at least partially countersunk into the plate portion 14, so as to provide a relatively smooth profile to the plate portion.

The plate portion 14 also includes a screw hole 74 adjacent the neck portion 16 that is adapted to receive a jig screw 76 which couples a drill guide jig 78 (FIG. 10) over the device 10. Drill guides 80, 82 can be used through guide holes 84, 86, 87, 88 (not shown), 89 in the guide jig 78 to drill holes, from outside the bone, through the bone and in alignment with the screw holes 22, 24 and the peg holes 50, 52, 54.

Figure 11:
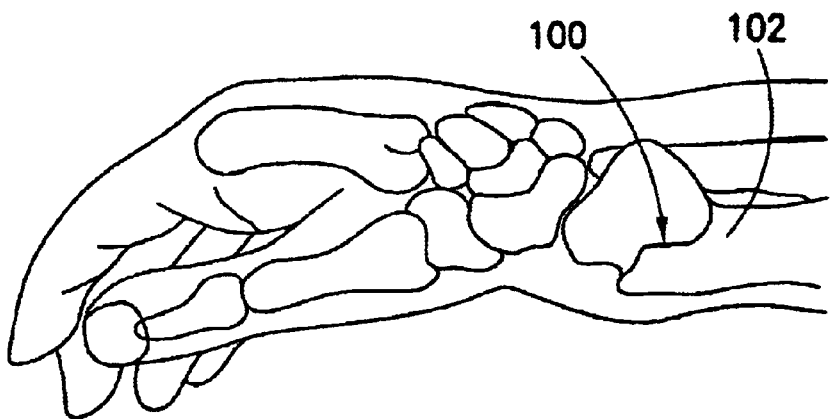
FIGS. 11 through 16 illustrate a method of using the fixation system of the invention to stabilize a fracture.
Figure 12:
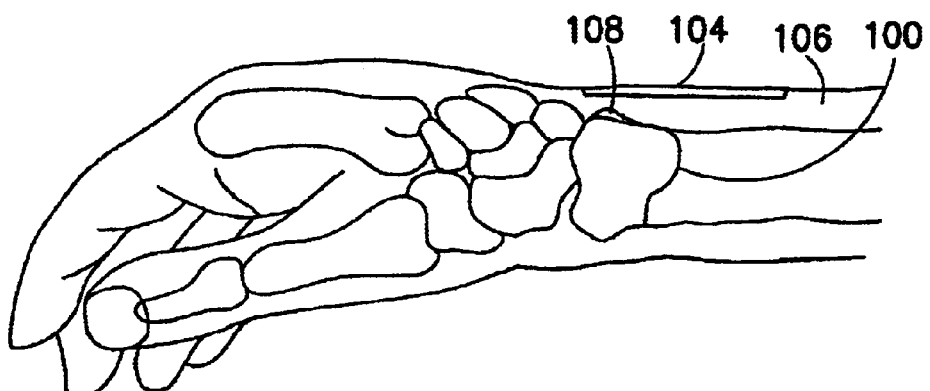
Figure 13:
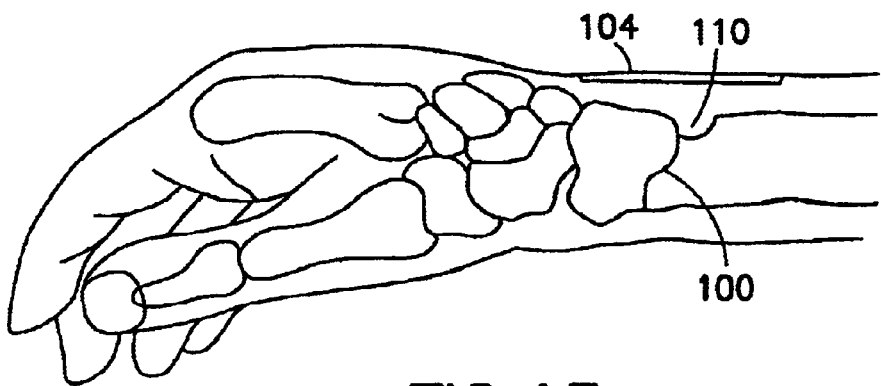

The device 10 is used as follows to treat a fracture 100 of the distal radial bone 102 (e.g., a Colles' fracture), as represented in FIG. 11. Referring to FIG. 12, first, a relatively small incision 104 (generally approximately 4 cm in length) is made in the skin 106 on the dorsal side of the fracture 100. For distal radial fractures, the incision is preferably at a location between the second and third extensor compartments and above Lister's tubercule 108 (a small bump a the distal end of the radius bone) so that the extensor tendons are not irritated by the incision or by the implanted device 10. Referring to FIG. 13, a rongeur (not shown) is then used to take small bites out of the bone at the broken end of the radius bone so that a notch 110 is created preferably on the proximal side of the distal radius fracture 100. In addition, at least a portion of Lister's tubercule is preferably removed to provide a surface for placement of the plate portion 14 at a location which will not cause tendon irritation.

Figure 14:
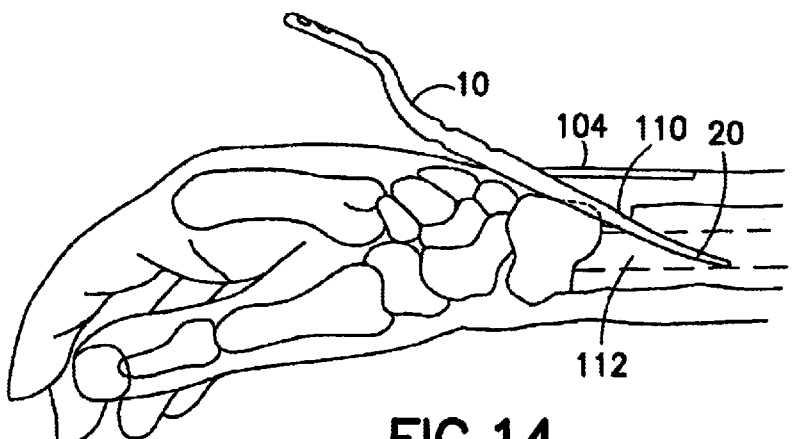

Referring to FIG. 14, the tapered resilient section 20 of the nail portion 12 of the device is then introduced percutaneously (via incision 104) through the notch 110 and into the medullary canal 112 of the bone. The nail portion 12 is pushed into the medullary canal 112 of the radius bone 102 until the neck portion 16 lies in the notch 110 created in the distal end of the bone and the plate portion 14 is positioned on the bone distal of the fracture and at the surface of the removed portion of Lister's tubercule. It is appreciated that reduction of the fracture (from the bone position of FIG. 11 to the bone position of FIGS. 12 through 15) may occur at this stage or at any other medically reasonable time during the fracture fixation process. During introduction into the bone and when implanted in the bone, the resilient section 20 is permitted to undergo some degree of bending, which may be necessitated if the entryway into the bone for the nail portion is too small of if the medullary canal is not be perfectly straight.

Figure 15:
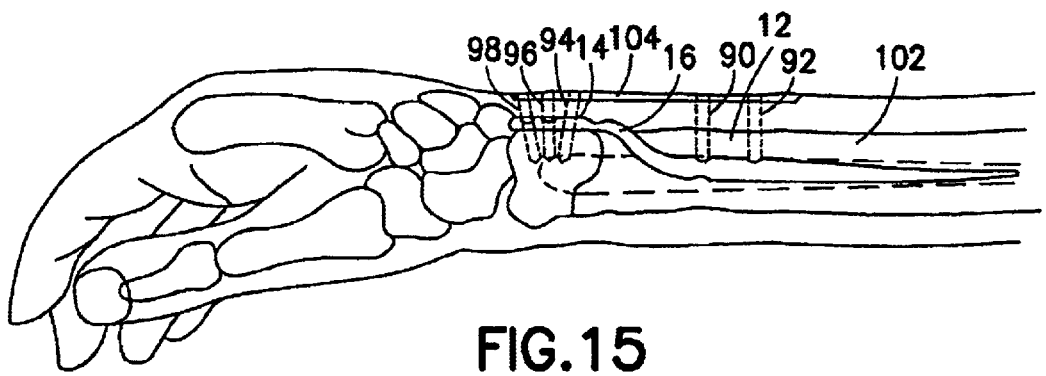

Referring to FIGS. 10 and 15, the jig 78 is then fixed to the device 10 at hole 74 with the guide screw 76, and the guides 80 and 82 are placed in the jig 78. The tissue (e.g., the muscle tissue and periosteum) over the bone and beneath the guide holes 84, 86 is relocated. Using a drill, holes 90, 92 are drilled through the guide 80 (which is positioned in each of guide holes 84 and 86) and into the near cortical bone into alignment with the screw holes 24, 26. In addition, holes 94, 96, 98 are drilled through guide 82 (which is positioned in each of guide holes 87, 88 (not shown), 89 in alignment with each of peg holes 50, 52, 54) and into the subchondral bone.

Figure 16:
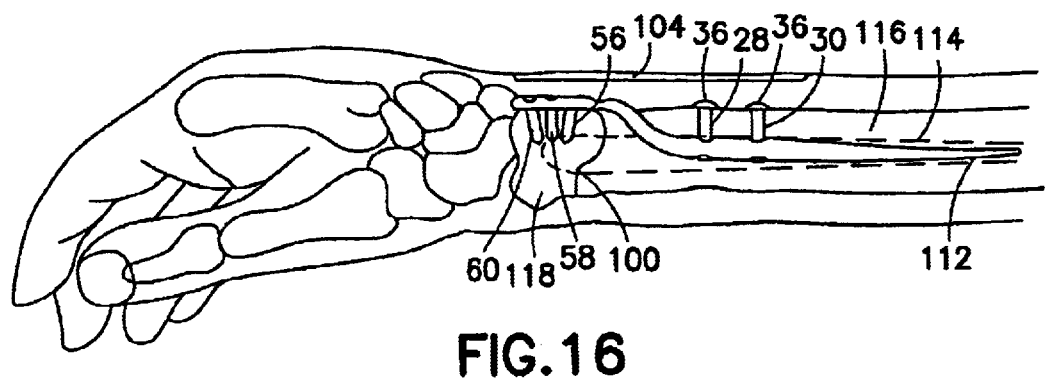

Referring to FIGS. 6, 6A and 16, the unicortical screws 28, 30 are then introduced through the drilled holes 90, 92 and into the screw holes 24, 26 in the nail portion 12. The distalmost screw 28 is preferably inserted first into screw hole 24 and tightened. The threaded channel 160 self-aligns the screw 28 in the screw hole 24 to prevent cross-threading. The body portion 152 of the screw 28 engages the screw hole 24, and the clearance portion 154 permits free rotation inside the cortical wall 116. Thus, as the screw 28 is rotated, the rigid portion 22 of the nail portion 12 functions as nut for the screw 28 and is pulled up against the interior surface 114 of the cortical bone. The thread channel 158 of the clearance portion 154 permits engagement of the rigid portion 22 of the nail portion 12 over a large range of cortical bone wall thicknesses. Thus, if the bone wall is thinner than the length of the clearance portion, the screw 28 can be further inserted which engagement is maintained between the screw and the screw hole. Then, the relatively proximal screw 30 is similarly inserted into the respective screw hole 26 and tightened. Tightening of both screws 28, 30 operates to pull the rigid portion 22 of the nail portion 12 against the inner surface 114 of the cortical bone 116 and into a desired alignment with respect to the medullary canal 112 of the bone. Moreover, due to the taper along the rigid portion 22 of the nail portion 12, upon tightening of the screws 28, 30, the entire device 10 is oriented in a slightly palmar direction such that the plate 14 is forced against the subchondral fragments 118 to facilitate reduction and stabilization of the fracture 100. Thus, the plate portion 14 is also thereby provided into a proper orientation for support of the metaphyseal area. In addition, as the screw heads 36 are relative large, the bone 116 is clamped between the screw heads 36 and the rigid section 22 of the nail portion 12, and stability of the device is increased. Alternatively, a combination of unicortical screws 28 and bicortical screws 40 (FIG. 7) can be used through respective screw holes such that the device is stably held. If bicortical screws are used, the tip thereof may be extended through a hole drilled in the far cortex, or the tip may extend to contact the inner surface of the far cortex.

The pegs 56, 58, 60 are then introduced through drilled holes 94, 96, 98 until the heads 66 of the pegs thread into the peg holes 50, 52, 54 of the plate portion 14 of the device 10. The pegs 56, 58, 60 provide stabilization and support for subchondral fragments, including the radial styloid and the volar dipunch. Moreover, the pegs preferably enter the subchondral fragments from a plurality of directions, providing additional fixation of the device 10 to the bone.

The fixation system permits a relatively minimally invasive treatment of long bone fractures that may otherwise be undertreated. In addition, such fixation is very stable due to the clamping of the bone between the large screw heads and the device. Moreover, the large screw heads distribute the stress on the bone over a relatively large surface area on the outer surface of the cortical bone.

When the device is used to treat a distal radial fracture, such as a Colles' fracture, particular dimensions are preferred, though the dimensions of the device are not limited thereto. Such preferred dimensions include an overall device length of approximately 4.2 inches, with the nail portion having a length of approximately 3.56 inches, and the plate portion having a length of approximately 0.65 inch. The bottom surface of the plate portion is preferably located approximately 0.29 inch above a longitudinal axis extending through the nail portion. The preferred length for the unicortical screws is preferably approximately 0.28 inch (under the head), and the length of the bicortical screws is preferably approximately 0.60 inch (under the head). The laterally extending first and second pegs 56, 58 are preferably approximately 1 inch in length, and the distalmost third peg 60 is preferably approximately 0.7 inch in length.

The fixation system can be adapted for treatment of fractures at multiple sites. For example, the distal radius, the proximal humerus, the distal femur, the proximal tibia, the distal tibia, and the hip are all suitable for application of the system of the invention, although the device and screws of the system may need to be dimensioned appropriately for the site of use.

There have been described and illustrated herein embodiments of a fixation device and a method of using the device to treat bone fractures. While particular embodiments of the invention have been described, it is not intended that the invention be limited thereto, as it is intended that the invention be as broad in scope as the art will allow and that the specification be read likewise. Thus, while particular dimensions have been disclosed, it will be appreciated that other dimensions may be used as well. In addition, while titanium and stainless steel are the preferred materials, it will be understood that other biocompatible materials can be used. Moreover, the resilient portion may be made from a different material than the rigid portion and/or the plate portion, and the two portions may then be joined. In addition, particular in application for larger bones, more than two machine screw holes and screws therefor may be used. Also, while three pegs are preferred, one or more pegs may be used, and more than three can be used in relatively larger devices. Furthermore, not all of the peg holes or screw holes need by provided with pegs and screws. However in accord with the invention, it is preferred that at least one peg and at least one screw are used in the fixation system. It will therefore be appreciated by those skilled in the art that yet other modifications could be made to the provided invention without deviating from its spirit and scope as claimed.

What is claimed is:

1. A bone fracture fixation device, comprising:
   a) an elongate nail portion including at least one threaded screw hole extending therein; and
   b) a plate portion including at least one threaded peg hole extending completely through the plate portion, said plate portion being parallel to but not coaxial with said nail portion.

2. A bone fracture fixation device according to claim 1, wherein:
   said nail portion includes at least two longitudinally displaced threaded screw holes which extend completely through the nail portion.

3. A bone fracture fixation device according to claim 1, wherein:
   said nail portion includes a relatively rigid portion and a relatively resilient portion, and said at least one screw hole is in said relatively rigid portion.

4. A bone fracture fixation device according to claim 1, wherein:
   said nail portion is straight.

5. A bone fracture fixation device according to claim 1, wherein:
   said nail portion is tapered.

6. A bone fracture fixation device according to claim 1, wherein:
   said nail portion has a circular cross-sectional shape.

7. A bone fracture fixation device according to claim 1, wherein:
   said plate portion includes a plurality of threaded peg holes.

8. A bone fracture fixation device according to claim 7, wherein:
   said plurality of threaded peg holes are longitudinally displaced in said plate portion.

9. A bone fracture fixation device according to claim 7, wherein:
   at least one of said plurality of threaded peg holes has an oblique axis relative to the others of said plurality of threaded peg holes.

10. A bone fracture fixation device according to claim 9, wherein:
    each of said threaded peg holes has an oblique axis relative to the others.

11. A bone fracture fixation device according to claim 1, wherein:
    said nail portion and said plate portion are longitudinally displaced relative to each other.

12. A bone fracture fixation device according to claim 1, wherein:
    said at least one threaded screw hole has a first thread pitch, said at least one threaded peg hole has a second thread pitch, and said first and second thread pitches are different.

13. A bone fracture fixation kit, comprising:
    a) a fixation device having an elongate intramedullary portion and a plate portion, said intramedullary portion including at least one threaded screw hole and said plate portion including at least one threaded peg hole;
    b) at least one machine screw having a shaft adapted to be threadably received in one of said at least one screw hole and having a head with a flat undersurface, said head being larger than said screw hole; and
    c) at least one peg having a threaded head and a shaft, said head adapted to be threadably engaged in one of said at least one threaded peg hole.

14. A kit according to claim 13, wherein:
    said at least one machine screw has a relatively blunt tip.

15. A kit according to claim 13, wherein:
    said at least one peg has a non-threaded shaft.

16. A kit according to claim 13, wherein:
    said plate portion includes a plurality of threaded peg holes each having an oblique axis relative to axes of the other peg holes.

17. A kit according to claim 13, wherein:
    said at least one machine screw includes screws of different lengths.

18. A bone fracture fixation system, comprising:
    a) a fixation device having an elongate intramedullary portion and a plate portion, said intramedullary portion including at least one threaded screw hole and said plate portion including at least one threaded peg hole;
    b) at least one machine screw having a shaft threadably engaged in said at least one screw hole and having a head with a flat undersurface, said head being larger than said screw hole; and
    c) at least one peg having a threaded head and a shaft, said head threadably engaged in said at least one threaded peg hole.

19. A fracture fixation system according to claim 18, wherein:

said plate portion includes a plurality of threaded peg holes each having an axis oblique relative to axes of the other peg holes, and said at least one peg includes a plurality of pegs, said shaft of each of said pegs extending coaxial with one of said axes of said peg holes.

20. A bone fracture fixation kit, comprising:
a) a metal fixation device having an elongate intramedullary portion including a threaded screw hole; and
b) a machine screw having a head and a shaft,
said head having a flat undersurface which is larger than said threaded screw hole, and
said shaft including a tip portion, a body portion, and a clearance portion between said body portion and said head, said body portion having threads adapted to be threadably engaged in said threaded screw hole and defining a first diameter across said threads, said clearance portion having a relatively smooth surface compared with said body portion and a second diameter smaller than said first diameter, and said tip portion having a relatively smooth surface compared with said body portion and a third diameter smaller than said second diameter.

21. A kit according to claim 20, wherein:
said tip portion includes a shallow thread channel continuous with and of the same pitch as said threads of said body portion.

22. A kit according to claim 20, wherein:
said clearance portion includes a shallow thread channel continuous with and of the same pitch as said threads of said body portion.

23. A bone fracture fixation system for fixation of a metaphyseal fracture of a long bone which defines subchondral bone fragments, the long bone having interior and exterior surfaces and a cortex with and an intramedullary region therethrough, said device comprising:
a) a rigid elongate structure adapted to extend within the intramedullary region of the bone;
b) a rigid plate structure adapted for placement on the exterior surface of the bone over the subchondral bone fragments, said plate structure being coupled to said elongate structure;
c) means for clamping said elongate structure against the interior surface of the bone; and
d) a framework of shaft-like elements coupled to said plate structure and extending in oblique axes relative to each other so as to provide support for subchondral bone fragments.

24. A bone fracture fixation system according to claim 23, wherein:
said shaft-like elements comprise pegs.

25. A method of stabilizing a metaphyseal bone fracture, the bone having interior and exterior surfaces and a cortex with and an intramedullary region and the fracture region defining subchondral fragments, comprising:
a) providing a fixation device having an intramedullary portion and an external portion, the intramedullary portion having at least one threaded hole screw hole and the external portion having a plurality of threaded peg holes;
b) inserting the intramedullary portion into the bone at a location adjacent the bone fracture;
c) manipulating the device to provide the intramedullary portion within the intramedullary region of the bone;
d) first drilling at least one hole through the cortex in alignment with the at least one screw hole;
e) second drilling a plurality of holes into at least one subchondral fragment in alignment with the peg holes, at least one of the drilled holes being oblique relative to the others;
f) first inserting at least one screw through the cortex and into the screw hole, the screw having a relatively large head with a substantially flat undersurface;
g) tightening the at least one screw to cause the cortex of the bone to be clamped between the intramedullary portion of the device and the undersurface of the head of the at least one screw;
h) reducing the fracture; and
i) second inserting a plurality of pegs through the plurality of holes drilled in said second drilling to provide support for subchondral fragments and threadably engaging the head of the at least one peg in the at least one peg hole.

26. A method according to claim 25, wherein:
said first inserting includes inserting a screw having a length adapted to extend through a near cortex of the bone and into the intramedullary portion of the device, but not into a far cortex of the bone.

27. A method according to claim 25, wherein:
said first inserting includes inserting first and second screws, said first screw having a first length, said second screw having a second length, and said first and second lengths being different from each other.

28. A method according to claim 25, wherein:
said second inserting occurs after said reducing the fracture.

29. A method according to claim 25, wherein:
said first inserting includes inserting at least one machine screw through the cortex and into the screw hole.

* * * * *